(12) United States Patent
Pöhlmann et al.

(10) Patent No.: US 9,738,592 B2
(45) Date of Patent: Aug. 22, 2017

(54) METHOD FOR REMOVING IMPURITIES FROM DINITROTOLUENES

(71) Applicant: Josef Meissner GmbH & Co. KG, Köln (DE)

(72) Inventors: Jürgen Pöhlmann, Köln (DE); Heinrich Hermann, Köln (DE); Mirko Händel, Neunkirchen-Seelscheid (DE); Jürgen Gebauer, Geldern (DE); Tim Bergmann, Köln (DE)

(73) Assignee: Josef Meissner GmbH & Co. KG, Köln (DE)

( * ) Notice: Subject to any disclaimer, the term of this patent is extended or adjusted under 35 U.S.C. 154(b) by 0 days.

(21) Appl. No.: 15/323,800

(22) PCT Filed: Apr. 30, 2015

(86) PCT No.: PCT/EP2015/059493
§ 371 (c)(1),
(2) Date: Jan. 4, 2017

(87) PCT Pub. No.: WO2016/005070
PCT Pub. Date: Jan. 14, 2016

(65) Prior Publication Data
US 2017/0166514 A1 Jun. 15, 2017

(30) Foreign Application Priority Data

Jul. 7, 2014 (DE) .......... 10 2014 009 948
Mar. 25, 2015 (DE) .......... 10 2015 003 743
Apr. 7, 2015 (DE) .......... 10 2015 004 242

(51) Int. Cl.
*C07C 201/16* (2006.01)
*B01D 11/04* (2006.01)
*B01D 19/00* (2006.01)
*B01J 19/24* (2006.01)
*C07C 205/06* (2006.01)

(52) U.S. Cl.
CPC ........ *C07C 201/16* (2013.01); *B01D 11/0488* (2013.01); *B01D 19/0005* (2013.01); *B01J 19/24* (2013.01); *B01J 2219/24* (2013.01); *Y02P 20/582* (2015.11)

(58) Field of Classification Search
CPC ..... C07C 201/16; C07C 205/06; B01D 11/04; B01D 19/00; B01J 2219/24
See application file for complete search history.

(56) References Cited

U.S. PATENT DOCUMENTS

2013/0041189 A1* 2/2013 Deckert ................ C07C 201/16
568/939

* cited by examiner

*Primary Examiner* — Jafar Parsa
(74) *Attorney, Agent, or Firm* — Edward E. Sowers; Brannon Sowers & Cracraft PC (57) ABSTRACT

The present invention relates to a method for purifying raw dinitrotoluenes resulting from dinitration of toluene in the presence of a nitric acid/sulfuric acid/nitrating acid mixture, and a device or plant for performing the method, and a corresponding production plant for producing dinitrotoluene, characterized in that (a) the raw dinitrotoluenes are first subjected to a wash with at least one washing medium after separation of the nitrating acid mixture, followed by a separation of the washing medium; and that (b) subsequently the washed dinitrotoluenes resulting from method step (a) are subjected to stripping (stripping gas treatment) with at least one gas (stripping gas).

10 Claims, 4 Drawing Sheets

METHOD FOR REMOVING IMPURITIES FROM DINITROTOLUENES

CROSS-REFERENCES TO RELATED APPLICATIONS

This application is a National Stage filing of International Application PCT/EP 2015/059493, filed Apr. 30, 2015, entitled METHOD FOR REMOVING IMPURITIES FROM DINITROTOLUENES, claiming priority to German Application Nos. DE 10 2014 009 948.2 filed Jul. 7, 2014; DE 10 2015 003 743.9 filed on Mar. 25, 2015; and DE 10 2015 004 242.4 filed on Apr. 7, 2015. The subject application claims priority to PCT/EP 2015/059493, DE 10 2014 009 948.2, DE 10 2015 003 743.9, and to DE 10 2015 004 242.4 and incorporates all by reference herein, in their entirety.

BACKGROUND OF THE INVENTION

The present invention relates to the technical field of nitration of toluene for preparation of dinitrotoluenes with subsequent removal of the impurities from the crude dinitrotoluenes (crude DNTs) for the purposes of providing pure dinitrotoluenes.

More particularly, the present invention relates to a process for purifying crude dinitrotoluenes that result from the nitration (dinitration) (e.g. adiabatic or isothermal nitration) of toluene in the presence of a nitric acid/sulfuric acid nitrating acid mixture (i.e., in other words, a process for preparing or providing pure or purified dinitrotoluenes), and a corresponding apparatus or plant for performing this process.

In addition, the present invention relates to a production plant for preparation of dinitrotoluenes (i.e. a production plant for nitration of toluene to dinitrotoluenes) with subsequent purification of the nitrated crude dinitrotoluenes formed in the nitration (crude DNTs).

Dinitrotoluenes (DNTs) are an important intermediate in the chemical industry, which, after reduction to the corresponding amines (for example by reaction with hydrogen in the presence of a catalyst), serve particularly as starting materials or reactants for polyurethanes.

In general, DNT is prepared as an isomer mixture by reacting toluene with nitric acid directly or in the presence of sulfuric acid as catalyst and water-binding agent in one stage or in two stages in countercurrent, isothermally or else adiabatically. After removal of the spent nitrating acid (i.e. generally a spent nitric acid/sulfuric acid nitrating acid mixture), a still variously contaminated crude dinitrotoluene is obtained, which is in a purity that allows further use or further processing only after passing through further, usually complex, treatment steps.

In the context of the present application, in relation to the dinitrotoluene(s) (DNT or DNTs), the singular or plural form is used synonymously hereinafter.

In the conversion of toluene to dinitrotoluene (DNT) with nitric acid, as well as the desired nitro species, a multitude of impurities, especially a multitude of very different by-products and other impurities, are present in the crude DNT, especially including traces of MNT (mononitrotoluene), TNT (trinitrotoluene) and residues of aliphatic and cycloaliphatic hydrocarbons that are always present in the starting toluene, and additionally a series of further by-products, for example mononitrocresols (MNK), dinitrocresols (DNK) and trinitrocresols (TNK), trinitrophenol (picric acid or PS), nitrobenzoic acids (NBS) such as mononitro-benzoic acid (MNBS) and dinitrobenzoic acid (DNBS), and degradation products from the oxidation of the aliphatic and cycloaliphatic hydrocarbons, and of the nitrocresols and nitroaromatics with the nitric acid from the mixed acid, for example carbon dioxide ($CO_2$), carbon monoxide (CO), hydrogen cyanide (HCN), tetranitromethane (TNM), formic acid, acetic acid, oxalic acid, etc., and reaction or reduction products of nitric acid, such as nitrogen oxides (e.g. nitrogen oxide NO, nitrogen dioxide $NO_2$, dinitrogen oxide $N_2O$, etc.), nitrous acid, etc. In addition, nitric acid and sulfuric acid are usually present in the crude DNT, especially in dissolved form and/or as a microemulsion of the spent nitrating acid in finely divided form.

In general, all these impurities or at least a significant portion thereof have to be removed from the crude DNT prior to the further processing or further use thereof. The extent of the contamination, i.e. the residual content of the impurities in the purified nitroaromatic, is determined especially by the levels of purity required based on the use, which depend upon factors including the process envisaged for the further use or the like. In particular, all substances that disrupt further processing, even in traces, have to be reduced to a minimum, for example the hydrogenation-preventing substances, for example sulfur compounds, nitrogen oxides, nitric acid etc. (cf., for example, U.S. Pat. No. 4,224,249 A), nitrocresols (cf., for example, U.S. Pat. No. 2,976,320 A), carbon dioxide (cf. EP 1 935 870 A1), sodium ions or the known complexing agents and catalyst poisons, for example CO, $N_2O$, hydrogen cyanide, etc.

According to the prior art, these impurities are typically removed from the crude nitroaromatics (crude DNTs) after separation (removal) of the spent nitrating acid by a wash in a plurality of wash steps before the nitroaromatic is sent to a direct use, an isomer separation or a hydrogenation to the corresponding amines.

Typically, the wash of the crude nitroaromatics for the removal of the acids which are dissolved and suspended in the nitration mixture, of the nitrophenols and of other acidic and other impurities that are still extractable with the washing agent consists of three steps (see, for example, F. Meissner et al., Industrial and Engineering Chemistry Vol. 46, 721 (1954); Ullmanns Enzyklopädie der technischen Chemie [Ullmann's Encyclopedia of Industrial Chemistry], 4th edition, vol. 17, pages 385/386; H. Hermann et al., ACS Symposium Series 632, 238 (1996), page 241 [editors: L. F. Albright, R. V. C. Carr, R. J. Schmitt]; A. B. Quakenbush et al., The Olin Dinitrotoluene (DNT) Process, Polyurethanes World Congress 1993, Publish: Technomic Lancaster, pages 484-488; U.S. Pat. No. 6,288,289 B1; EP 1 816 117 A1).

This three-stage wash of the crude nitroaromatics generally comprises the following wash steps:

1. Wash Step I or Acidic Wash:
   Wash with water (acidified as a result of the spent nitrating acid mixture), especially for removal of the dissolved and suspended strong mineral acids, such as sulfuric acid and nitric acid, and the nitroses (i.e. nitrogen oxides).
2. Wash Step II or Alkali Wash (Basic Wash):
   Wash in the presence of a base, for example sodium carbonate (soda), sodium bicarbonate, sodium sulfite or sodium hydrogensulfite, ammonia, sodium hydroxide solution, potassium hydroxide solution etc. (cf., for example, U.S. Pat. No. 4,482,769 A, U.S. Pat. No. 4,597,875 A or U.S. Pat. No. 6,288,289 B1), especially for removal of traces of nitric acid, nitrogen oxides and sulfuric acid that are still present in dissolved and suspended form in the nitroaromatics after wash step I, and of weakly acidic impurities still dissolved in the nitroaromatics, such as nitrophenols, nitrocresols, nitrobenzoic acids, degradation products from the oxidative breakdown of phenols or aliphatic and/or cyclic hydrocarbons, etc., for example hydrogen cyanide, oxalic acid, formic acid, acetic acid, etc.

3. Wash Step III or Neutral Wash:

Neutral wash, especially for removal of the residual traces of alkalis or basic compounds from microemulsion or other entrainment from wash step II, and for further reduction of the impurities still present in traces in the product.

It is possible in principle for every wash step to comprise up to 10 extraction stages in cross- or countercurrent or a combination thereof, as described, for example, in CA 1 034 603, in EP 1 780 195 A1, in U.S. Pat. No. 6,288,289 B1 or in WO 2013/160367 A1.

The wash medium used for the wash is typically water. In general, the wash is conducted as a liquid/liquid extraction, i.e. at temperatures where the nitroaromatic to be washed is in liquid form.

The aim of this generally multistage wash is to obtain, apart from a pure product which can be processed further without any adverse effect resulting from impurities still present, a minimum amount of wastewater per metric ton of product, by washing out the impurities that are present in such a manner that the disposal thereof can be conducted inexpensively, advantageously with recovery or recycling of unconverted reactants.

In the washing of the crude DNTs with water in the context of a liquid/liquid extraction, however, impurities washed out are predominantly only those which have a high solubility in the wash medium (for example sulfuric acid and nitric acid) or which disproportionate in the aqueous medium with the water to give nitric acid or which form salts with the bases added within the alkaline or basic wash (see wash step II above) and hence are removed irreversibly from their partition equilibrium with the DNT organic phase (for example residual traces of the strong acids [sulfuric acid and nitric acid] and the medium-strength and weak acids [for example nitrophenols, nitrocresols, nitrobenzoic acids, acetic acid, oxalic acid, formic acid, carbonic acid, hydrogen cyanide, etc.]). But even in relation to these impurities, the removal thereof in the wash is not always complete or quantitative, especially not when the crude DNTs have high loadings of impurities.

It has also been found, moreover, that other impurities, especially impurities having unfavorable partition coefficients in relation to the wash medium, impurities with weak or zero acidity and impurities having a slow conversion rate to such substances that do not dissolve in the organic phase, often cannot be removed completely with a wash having one or more steps in the context of a liquid/liquid extraction and/or can be removed only with a high level of technical complexity. This is true particularly when, for reasons of process economy (especially for reduction of the wastewater burden), the wash in the individual wash steps is effected with a ratio of wash medium used to washing nitroaromatic of less than 1 (for example at a volume ratio in the range from 1:5 to 1:20), even when the ratio of wash medium to nitroaromatic in the wash apparatus, through circulation of the wash medium, is 1 or even greater than 1. Such impurities that can be removed only with difficulty or only incompletely in the context of a wash typically include, but are not limited to, nitrogen oxides $NO_X$ (e.g. nitrogen oxide NO, nitrogen dioxide $NO_2$, dinitrogen oxide $N_2O$ etc.), hydrogen cyanide, aliphatic and aromatic hydrocarbons, carbon oxides (CO, $CO_2$ etc.) etc.

More particularly, it is found to be difficult to remove the impurities from the crude DNTs when only one wash step is used, for example an acidic wash only. As described in CA 1 034 603, U.S. Pat. No. 4,224,249 A, EP 0 297 312 A1, EP 0 736 514 A1 or EP 1 780 195 A1, the washed DNT still contains, as well as traces of the strong acids sulfuric acid, nitric acid and nitrogen oxides $NO_X$, all medium-strength and weak organic and inorganic acids having $pK_A$ values equal to or greater than the pH of the wash acid, for example nitrocresols, nitrobenzoic acids, hydrogen cyanide, $CO_2$, etc., and additionally also all neutral or nonacidic impurities, for example CO, $N_2O$, hydrocarbons, etc., which, according to their solubility in the wash acid and depending on their individual partition equilibrium, are only partly washed out and hence remain in the DNT. It is particularly difficult here to remove the nitric acid, since $NO_X$ which is constantly dissolved in small amounts in the DNT, in the presence of traces of dispersed water, constantly reforms nitric acid.

According to CA 1 034 603, seven washes with water in crosscurrent (example 2) are required in order to attain a residual content of mineral acids in the DNT of about 15 ppm. The medium-strength and weak inorganic and organic acids remain in the organic phase at pH values less than 4 (after 7 water washes) and are extracted into the wash medium only in accordance with their partition equilibria.

According to U.S. Pat. No. 4,224,249 A, a DNT washed only with water contains less than 6000 ppm of total acidity and preferably less than 3000 ppm (calculated as sulfuric acid) of acids. Of this, 1100 ppm is nitrate, 160 ppm is nitrite and 230 ppm is sulfate. All weak acids, such as nitrocresols, and all neutral impurities, by contrast, remain in the DNT.

EP 0 297 312 A1, EP 0 736 514 A1 and EP 1 780 195 A1 disclose processes which permit conduction specifically of the wash step of the acidic wash so as to obtain a wash acid with maximum concentration of acid (a mixture of sulfuric acid, nitric acid and nitrous acid or $NO_X$). This wash acid is recycled into the nitration directly or preferably after concentration to a total acid (calculated as nitric acid) of 50% to 60%. In order to achieve this enrichment of the sulfuric and nitric acid in the wash acid, the ratio of DNT to fresh water must be very high. Thus, in the working example of EP 0 736 514 A1, one metric ton of crude DNT is washed in multiple stages in countercurrent with about 110 liters of fresh water (corresponding to a ratio of DNT to fresh water of 9.1:1), in order to obtain a wash acid with about 23.3% total acid (corresponding to an amount of wash acid of about 142 kg per metric ton of DNT). With a ratio of DNT to fresh water for the acidic wash of about 13:1, only about 77 liters of fresh water would be required per metric ton of crude DNT to be washed, and a wash acid with more than 30% total acid would be obtained.

Given such a phase ratio of DNT to water of about 9:1 or 13:1, with impurities having extraction factors ϵ of 1 or less and partition coefficients in favor of the extractant of 10 or less, exhaustive extraction with extraction yields of 90% or more is enabled only as a result of a very high to theoretically infinite number of extraction stages (in this regard, cf., for example, K. Sattler, Thermische Trennverfahren [Thermal Separation Processes], Wiley-VCH publishers, 3rd edition 2001, pages 545 ff.); this is extremely technically demanding and very costly and, moreover, is not technically possible in the case of impurities having partition coefficients less than 5.

By contrast, by such a conventional one-stage or multistage wash in the form of a liquid/liquid extraction as described, for example, in the prior art according to EP 0 297 312 A1, EP 0 736 514 A1 and EP 1 780 195 A1, it is not possible to remove impurities having unfavorable partition coefficients in relation to the wash medium, impurities having low solubility in the wash medium, impurities having weak or zero acidity and impurities having a slow conversion rate to substances that do not dissolve in the organic phase from the crude DNT, or not possible to do so completely and efficiently. The impurities that cannot be removed in this way include, for example (but without restriction), nitrogen oxides $NO_X$, carbon oxides such as CO and $CO_2$, hydrogen cyanide, hydrocarbons, etc.

Even by a wash of crude DNTs in three wash steps each having up to 5 extraction stages according to the prior art, wherein a wash step is conducted in the presence of a base, preferably sodium carbonate, at a pH in the range from 8.5 to 9.2, only weak mineral acids such as carbonic acid, and nitrophenols and nitrocresols, and organic acids such as nitrobenzoic acids, acetic acid, oxalic acid, formic acid etc., having $pK_A$ values below 7 are washed out more or less quantitatively. But even hydrogen cyanide with a $pK_A$ of about 9.2, in the case of the standard wash with sodium carbonate in the pH range of 8.5 to 9.2, is extracted only partly from the crude DNT; the aromatic and aliphatic hydrocarbons and CO, $N_2O$ etc. can be removed by extraction only according to their solubilities and partition equilibria from the crude DNT. The same applies when ammonia in excess is used as base; traces thereof may then additionally be present in the washed DNT.

A wash to improve the extraction level of impurities with unfavorable partition coefficients and/or with low solubility in the wash medium or of impurities with weak or zero acidity (such as $CO_2$, hydrogen cyanide, CO, $N_2O$ etc.) or of volatile or low-boiling aliphatic and aromatic hydrocarbons (such as hexane, pentane, cyclohexane, methylcyclohexane, dimethylcyclohexane, toluene etc.) or impurities having slow conversion rates to substances which no longer dissolve in the organic phase (such as $NO_X$ at low concentrations etc.) requires a high number of wash or extraction stages in countercurrent or else in crosscurrent or a combination thereof, associated with a disproportionately high extra consumption of wash medium and consequently extra occurrence of wastewater, which in turn leads to unacceptable capital and operating costs.

In addition, EP 0 897 907 B1 describes a process for recovering nitric acid into a mixture of aromatic compounds, wherein two supplementary process steps are to be used for purification of the crude nitration products: the crude nitration products, according to EP 0 897 907 B1, prior to the actual wash, are subjected to a distillation or a stripping operation for removal of the nitric acid, in order to remove the nitric acid dissolved or suspended in the crude nitration products prior to the wash in an at least partly separate manner and recycle it after appropriate treatment. However, this process, compared to the prior art outlined above, for purification of crude nitration products, requires considerable additional technical complexity, without being able to achieve an improved product purity compared to the prior art outlined above. As well as the waste stream from the downstream wash which is always still necessary (i.e. generally two waste streams from the wash, mainly wash acid from the acidic wash and wash alkali from the basic wash), the upstream step of distillation or stripping generates an additional third waste stream comprising dilute nitric acid, which has to be processed separately. If the waste stream from the wash and from the upstream distillation or stripping stage are combined for the purposes of common further processing, as well as the elevated technical complexity, there is no longer any advantage compared to a wash according to prior art. The upstream distillation or stripping, moreover, serves exclusively for nitric acid removal and recovery, but does not enable any improvement in relation to the removal of the impurities that are difficult to remove from the crude nitration products. Nor is there any focus on the peculiarities as occur specifically in the purification of crude dinitrotoluenes, but merely a quite general emphasis on the dinitration of any desired aromatic compounds. Moreover, the process proposed in EP 0 897 907 B1 constitute an elevated safety risk compared to the prior art and is therefore unsuitable especially for the purification of crude DNTs: given a content of up to 10% nitric acid in the crude nitration products and at temperatures up to 130° C. in the proposed distillation, oxidative and uncontrolled breakdown of the impurities present in the crude nitration products (for example nitrocresols, nitrobenzoic acids etc.), and also of DNT itself, cannot be ruled out with certainty. The process described therein is consequently unsuitable for the efficient and safe purification specifically of crude dinitrotoluenes. More particularly, it is not possible by the process described therein to remove trace impurities in order to produce high-purity DNT.

BRIEF SUMMARY OF THE INVENTION

There is thus no known process from the overall prior art by which it is possible in an efficient, process-economical and technically simple manner to completely remove impurities of all kinds from crude dinitrotoluenes (crude DNTs) which originate from the dinitration of toluene in the presence of a nitric acid/sulfuric acid nitrating acid mixture, especially impurities removable only with difficulty or only incompletely within the scope of a conventional wash (i.e. especially impurities having unfavorable partition coefficients in relation to the wash medium, impurities having weak or zero acidity and impurities having a slow conversion rate to such substances that do not dissolve in the organic phase).

It is therefore an object of the present invention to provide a process and an apparatus (plant) for purification of crude dinitrotoluenes (crude DNTs) that result from the nitration of toluene, wherein the drawbacks and inadequacies of the prior art outlined above are to be at least substantially avoided or else at least attenuated. Through the present invention, it is to be possible in a technically efficient and safe and simple manner to provide high-purity or purified dinitrotoluenes (DNTs). More particularly, it shall also be possible by the present invention to be able to effectively remove impurities that are difficult to remove, especially volatile impurities, from the crude DNTs.

More particularly, it is an object of the present invention to provide a process and an apparatus or plant suitable for performing this process, by which efficient purification of the nitrated crude products as originate from the nitration (dinitration) of toluene in the presence of a nitric acid/sulfuric acid nitrating acid mixture after removal of what is called the spent nitrating acid mixture is to be enabled.

In addition, it is an object of the present invention to provide a process and an apparatus for performing this process, which are to enable purification of crude dinitrotoluenes (DNTs) originating from an adiabatic or isothermal dinitration of toluene in a safer manner and with a minimum level of technical complexity, such that the content of impurities in the DNTs is reduced to such an extent that the specifications for a technical DNT quality (so-called "technical grade DNT") are attained or if possible surpassed. More particularly, such a process and such an apparatus shall enable efficient removability even of the considerable amounts of impurities, some of them removable only with difficulty (for example volatile impurities such as nitrogen oxides, nitric acid, nitrous acid, hydrogen cyanide, etc.), that are still present after the wash of the crude DNTs with a wash medium.

The objective outlined above is achieved in accordance with the invention by a process as described herein; further, advantageous developments and configurations of the process of the invention are similarly described.

The present invention further provides an apparatus or plant as described below along with further advantageous developments.

The present invention additionally provides a production plant in addition to further advantageous developments and configurations of this aspect of the invention.

It will be apparent that configurations, embodiments, advantages or the like which are cited only for one aspect of the invention hereinafter—for the purpose of avoiding unnecessary repetition—do of course also apply correspondingly in relation to all the other aspects of the invention.

It will additionally be apparent that, even in the case of subsequent statement of values, numbers and ranges, the values, numbers and ranges stated in this regard should not be considered to be restrictive; it will be apparent to the person skilled in the art that, depending on the individual case or on the basis of the application, it is possible to depart from the ranges and figures specified, without leaving the scope of the present invention.

Moreover, all the values or parameters or the like that are specified hereinafter can be ascertained or determined by standardized or explicitly specified determination methods or else by determination or analysis methods that are familiar per se to the person skilled in the art in this field.

With these provisos, the present invention is described in detail hereinafter.

DETAILED DESCRIPTION OF THE INVENTION

The present invention—in a first aspect of the present invention—thus provides a process for purifying crude dinitrotoluenes resulting from the nitration (i.e. dinitration) of toluene in the presence of a nitric acid/sulfuric acid nitrating acid mixture, especially for removing also particularly volatile impurities from the crude dinitrotoluenes, wherein, in the process, (a) the crude dinitrotoluenes, after separation from the spent nitrating acid mixture, are first subjected to a washing with at least one wash medium, followed by a removal of the wash medium (i.e. of the wash medium which is spent/used/laden with impurities); and (b) subsequently, the washed dinitrotoluenes that result from process step (a) are subjected to a stripping (stripping gas treatment) with at least one gas (stripping gas).

The process of the invention is outstandingly suitable for purification of crude dinitrotoluenes (crude DNTs) resulting from the nitration (dinitration) of toluene in the presence of a nitric acid/sulfuric acid nitrating acid mixture, especially for efficient removal of impurities that are otherwise difficult to remove, especially volatile, weakly acidic or neutral impurities having a low boiling point compared to DNT (for example nitrogen oxides such as nitrogen monoxide $N_2O$ inter alia, carbon monoxide, carbon dioxide, hydrogen cyanide, tetranitromethane, aliphatic and aromatic hydrocarbons etc.). But even other impurities, some of which are present only partly in traces, and which can be removed only partly or only incompletely, if at all, within the wash (for example nitric acid, water etc.) are removed efficiently.

It will be apparent that, within the scope of the overall process of the invention, at least essentially all impurities present in the crude dinitrotoluenes can be removed, irrespective of which impurities they are, especially irrespective of their volatilities, acidities, partition or extraction coefficients in relation to the wash medium or the like. The typical impurities, listed without restriction, which are present in the crude dinitrotoluenes that originate from the toluene nitration and which can be removed at least essentially completely in an efficient manner within the scope of the process of the invention include, for example, traces of the aliphatic and cycloaliphatic hydrocarbons always present in the starting toluene to be nitrated and the oxidative degradation products thereof, nitrocresols (mono-, di- and trinitrocresols), trinitrophenols or picric acid, nitrobenzoic acids (mono- and dinitrobenzoic acid) and degradation products from the oxidation of the aforementioned hydrocarbons, the nitrocresols and nitroaromatics for example carbon oxides (carbon monoxide and carbon dioxide), hydrogen cyanide, tetranitromethane, formic acid, acetic acid, oxalic acid etc., and additionally reaction products of nitric acid, such as nitrogen oxides (nitrogen monoxide, dinitrogen monoxide, nitrogen dioxide etc.); in addition, nitric acid, nitrous acid and sulfuric acid are additionally still present in the crude dinitrotoluenes, especially in dissolved or emulsified/finely dispersed form.

In the context of the present invention, it is possible in an efficient and process-economical manner not just to remove those impurities which have a high solubility in the wash medium or which disproportionate in the aqueous medium with the water to give nitric acid or which form salts with the bases added within the alkaline or basic wash and hence are removed irreversibly from their partition equilibrium with the DNT organic phase, but additionally also the impurities that are removable only with difficulty or only incompletely within a conventional wash, namely, in particular, impurities having unfavorable partition coefficients in relation to the wash medium, impurities having weak or zero acidity and impurities having a slow conversion rate to such substances that do not dissolve in the organic phase.

All the aforementioned impurities can be at least essentially completely removed within the scope of the process of the invention, the applicant having found that, surprisingly, this is possible only when the process step (b) of stripping gas treatment or stripping which is envisaged in accordance with the invention is conducted in addition to a wash of the crude dinitrotoluenes as per process step (a) and when, in particular, the stripping gas treatment follows downstream of the wash of the crude dinitrotoluenes. As the applicant has likewise surprisingly found, a reversal of the performance of the two process steps, by contrast, does not lead to the desired results (in other words, in this case, no efficient removal of all impurities takes place). Only by a stripping gas treatment downstream of the wash is it surprisingly possible also to achieve a removal of trace impurities as well to obtain pure DNTs.

The principle of the process of the invention is thus to subject the crude dinitrotoluenes that come from the nitration and still contain significant amounts of impurities—after removal of the spent nitrating acid or the spent nitrating acid mixture (for example in a separator etc.)—first to a wash with a wash medium, with subsequent removal of the wash medium, and subsequently to subject the dinitrotoluenes washed in this way to a stripping gas treatment (i.e. stripping with at least one gas or stripping gas).

This is because, as the applicant has found, completely surprisingly, the effect of performance of a stripping downstream of the wash is that at least essentially all impurities still present after the wash, especially impurities that are otherwise removable only with difficulty, for example the aforementioned volatile impurities, can be removed in an efficient, simple and safe manner. As the applicant has likewise found, even after a wash of the crude dinitrotoluenes conducted in several steps, considerable amounts of impurities, some of them removable only with difficulty, are still present in the dinitrotoluenes, and these can be removed effectively by the stripping in accordance with the invention.

As the applicant has likewise found, completely surprisingly, only the inventive combination of upstream wash and downstream stripping gas treatment (stripping) brings about effective purification of crude dinitrotoluenes resulting from the nitration of toluene—and only does so when the procedure is in the inventive sequence of process steps (i.e. the stripping downstream of the wash treatment or the wash step). Surprisingly, it is possible in this way to at least essentially completely remove even trace contaminations of impurities otherwise removable only with very great difficulty, if at all (e.g. hydrogen cyanide etc.).

By contrast with the prior art, more extensive, complex process steps for purification of the crude dinitrotoluenes in an efficient manner are avoided, without having to accept losses of quality in the purification of the crude dinitrotoluenes.

Surprisingly, the stripping gas treatment or stripping downstream of the wash ensures safe and simple or efficient removal of impurities still present, even in the trace region. Furthermore, the stripping gas treatment or stripping equally (depending on the loading of the stripping gas with water) brings about more or less extensive removal of the residual water still present (for example in dissolved or suspended form) in the dinitrotoluenes to be treated, meaning that this residual water can be effectively removed or at least significantly reduced.

In the context of the invention, an easily manageable process for purifying crude dinitrotoluenes resulting from the nitration of toluene is thus provided. In other words, in the context of the present invention, a process for providing or preparing purified or pure (high-purity) dinitrotoluenes (DNTs) is provided.

In a typical embodiment of the present invention, the present invention thus relates, more particularly, to a process for obtaining pure dinitrotoluene (DNT) as an isomer mixture or else as a pure isomer proceeding from crude DNT which is obtained from an isothermal or adiabatic reaction of toluene with nitric acid in the presence of sulfuric acid. After removing the spent nitrating acid, the crude DNT is contacted by a treatment with a wash medium (generally water) in one or more wash steps and washed in this way (typically, in the case of a plurality of wash steps, also with performance of one wash step in the presence of a base, especially at a pH in the range from 8 to 12), and—after removal of the wash medium—the water-washed DNT is subsequently treated with a stripping gas.

With regard to process step (a) (i.e. the wash step) of the process of the invention, the following should be noted in this regard:

Typically, the wash is conducted as what is called a liquid/liquid extraction.

In the present invention, within the scope of the process of the invention, in process step (a), the wash can be conducted in one or more wash steps, especially in one, two or three wash steps. Each wash step may in turn comprise one or more wash and/or extraction stages or each wash step can be conducted in one or more stages, especially one, two or three stages (where the wash and/or extraction stages can be conducted in crosscurrent and/or in countercurrent or a combination thereof).

In process step (a), the wash can typically be effected with a water-based wash medium. The water-based wash medium may be neutral, acidic or basic (alkaline).

In the process of the invention, in process step (a), the wash medium used may be a wash acid, an aqueous base or water.

In a preferred embodiment of the present invention, in the process, in process step (a), the wash can be conducted in three steps and/or in three wash steps. In this case, the three-step wash or the wash having three wash steps may comprise a first acidic wash step ("acidic wash step" or "acidic wash"), a subsequent second basic (alkaline) wash step ("basic or alkaline wash step" or "basic or alkaline wash") and a final third neutral wash step ("neutral wash step" or "neutral wash"). In this regard, reference may be made to the prior art outlined above with regard to the washing of nitrated crude products.

In a particular embodiment of the process of the invention, in process step (a), the wash (in each wash step in the case of two or more wash steps) can be conducted in crosscurrent or in countercurrent or else in a combination of cross- and countercurrent. The wash medium can advantageously be recycled.

At the end of process step (a), the spent wash medium is separated from the dinitrotoluenes washed with the wash medium. In general, in process step (a), the separation of the wash medium is conducted by means of a separating apparatus (separator), especially a static separating apparatus, or by means of a centrifugal separator. Alternatively, the phase separation can also be effected by means of other units or apparatuses that promote phase separation (e.g. coalescers etc.).

This is because the washed DNTs obtained after a wash with water, after removal of the wash medium, are always saturated with water and still contain traces of undissolved water in the form of a microemulsion. The DNTs obtained after static separation after a wash therefore usually have greater or lesser turbidity. In order to minimize the water content in the DNTs to be treated subsequently by means of stripping and hence to reduce the burden on the stripping, it is therefore possible—as already explained above—after the wash and prior to feeding of the DNTs into the stripping unit, to reduce the water content in the DNTs to the water dissolved in the DNTs, especially by means of a centrifugal separator etc.

Suitable processes and apparatuses (plants) for performance of the wash conducted in process step (a) are in principle known as such from the prior art and are described, for example (and without restriction) in the following documents originating from the same applicant: DE 195 12 114 A1 with patent family equivalents EP 0 736 514 A1 and U.S. Pat. No. 5,756,867 A; DE 10 2005 050 106 A1 with patent family equivalents EP 1 780 195 A1 and US 2007/088183 A1; and DE 10 2012 009 787 A1 with patent family equivalents WO 2012/156095 A1 and CA 2 835 121 A1.

With regard to process step (b) of the process of the invention, which follows process step (a), a stripping gas treatment is undertaken within this process step, meaning that the washed dinitrotoluenes resulting from process step (a) are subjected to stripping with at least one gas (stripping gas). As outlined above, it is possible in this way for the impurities still present after the wash, some of them being difficult to remove, especially volatile impurities, to be removed efficiently and effectively.

Stripping (also referred to synonymously as stripping gas treatment, stripping etc.) is a physical separation method in which, in general, substances (here: impurities) are selectively transferred from a liquid phase (here: DNTs) by desorption operations, especially with exploitation of Henry's law, to the gas phase. For this purpose, in general, the liquid phase is contacted with a gas (stripping gas) by the counter- and/or crosscurrent principle, preferably by the countercurrent principle.

In stripping, a form of desorption, the impurities to be removed are thus transferred physically from a liquid phase (DNT phase) to the gas phase, generally by contacting the liquid phase in counter- and/or crosscurrent with a much greater volume flow rate of gas (stripping gas).

The driving force behind the stripping process is that the vapor pressure of the substances or impurities to be removed from the liquid is greater in the liquid than in the gas (stripping gas), and liquid is therefore transferred into the gas (stripping gas).

As outlined hereinafter, the industrial performance of stripping is generally executed in suitable stripping apparatus, for example stripping columns, it being possible to adjust the stripping gas treatment with a view to the aim and/or effectively to tailor it by adjusting the apparatus features and the stripping conditions to the contaminated crude products to be treated. For further details in this regard, reference may be made, for example—in a nonrestrictive manner—to RÖMPP Chemielexikon [Chemical Dictionary], 10th edition, Georg-Thieme-Verlag Stuttgart/New York, 1996-1999, volume 5, page 4281, under the heading: "Strippen" [stripping], and volume 2, page 1470, under the heading: "Gasreinigung" [gas purification], and to Ullmanns Enzyklopädie der technischen Chemie, 4th edition, vol. 2, pages 575 ff., and to the literature reference in each case, all the aforementioned literature references hereby being fully incorporated by reference.

As detailed above, the stripping or stripping gas treatment is conducted in stripping apparatuses suitable for the purpose. Suitable apparatus for this purpose is especially any which permits generation of a large exchange area between stripping gas on the one hand and DNTs (which are liquid under stripping conditions) on the other hand.

More particularly, in process step (b), the stripping can be conducted in a stripping apparatus, wherein the stripping apparatus used may be a stripping column, especially a single-stage or multistage stripping column, preferably a column having random packings, sieve trays or bubble caps or a falling-film column or combinations thereof, or else a thin-film evaporator, a gas/liquid reactor or a horizontal stripping apparatus.

In principle, in process step (b), the stripping can be effected in cross- and/or countercurrent, preferably in countercurrent, and stripping gas in process step (b) can be conducted in cross- and/or countercurrent, preferably in countercurrent.

In a particular embodiment of the present invention, in process step (b), the stripping can be effected in multiple stages. In each of the various stripping stages, the stripping can be effected in cross- or countercurrent, preferably in countercurrent, or the stripping gas can be conducted in cross- or countercurrent, preferably in countercurrent, in each of the various stripping stages.

In order to enable efficient performance of the stripping gas treatment in process step (b), in process step (b) of the process of the invention, the stripping is conducted at temperatures above the melting temperature of the dinitrotoluenes, especially at a temperature of at least 56° C., preferably at a temperature of at least 60° C., more preferably at a temperature of at least 65° C. More preferably, in process step (b), the stripping is conducted within a temperature range from 56° C. to 130° C., especially within a temperature range from 65° C. to 105° C., preferably within a temperature range from 70° C. to 95° C.

In order to ensure that the stripping is effected at temperatures above the melting point of the dinitrotoluenes, it is advisable when, in process step (b), the stripping gas is used and/or contacted with the dinitrotoluenes with a stripping gas temperature within the range from 65° C. to 140° C., especially within the range from 70° C. to 120° C., preferably within the range from 70° C. to 95° C. For this purpose, in process step (b), the stripping gas on feeding into the stripping apparatus should have a temperature within the range from 65° C. to 140° C., especially within the range from 70° C. to 120° C., preferably within the range from 70° C. to 95° C.

The upper temperature which should not be exceeded in the stripping of the DNTs arises from safety considerations in particular. Since the DNTs should be in molten form in the course of stripping, it is advisable to conduct a safe and effective treatment of the DNTs with a stripping gas within a temperature range for the DNTs to be treated in the range from 56° C. to 130° C., preferably within the range from 65° C. to 105° C., more preferably within the range from 70° C. to 95° C. The lower temperature limit for the stripping is especially defined by the melting point of the DNTs and, for technical isomer mixtures, especially depending on the water content in the DNTs, is preferably in the range from 55° C. to 57° C. The temperature of the DNT melt after stripping should preferably not fall below 60° C. and should preferably be between 65° C. and 85° C., in order to reliably prevent deposition of DNT crystals (for example on the apparatuses or on their walls and pipelines). Accordingly, the temperature of the stripping gas should be within a range from 65° C. to 140° C., preferably within the range from 70° C. to 120° C., more preferably within the range from 70° C. to 95° C.

In general, the procedure in the context of the process of the invention is that, in process step (b), preferably over the entire process, the dinitrotoluenes are in the liquid state of matter and/or above their melting temperature and/or that, in process step (b), preferably over the entire process, the dinitrotoluenes have a temperature of at least 60° C. and preferably a temperature in the range from 56° C. to 130° C., especially in the range from 60° C. to 105° C., preferably in the range from 65° C. to 95° C., more preferably in the range from 65° C. to 85° C.

In order to prevent unwanted and hazardous heating of the DNTs above the upper temperature limit which is set for safety reasons, the DNTs in a DNT production plant are preferably not transported with standard pumps, and are instead only transported with conveying devices suitable for conveying of DNTs, for example centrifugal separators, which can also be used, for example, in the phase separation of DNTs, injectors etc., or else alternatively by gravimetric means.

In principle, the stripping gas treatment or stripping can be conducted not just within a wide temperature range but also within a wide pressure range, but always with the proviso that, in the stripping or stripping gas treatment, the DNTs to be treated should be in the liquid state of matter.

In principle, in process step (b), the stripping can be conducted at atmospheric pressure (standard pressure; 1.01325 bar) or else under vacuum (reduced pressure) or else at elevated pressure, preferably at atmospheric pressure. In general, in process step (b), the stripping can be conducted at an absolute pressure within the range from 0.2 bar to 3 bar, especially within the range from 0.3 bar to 1.2 bar, preferably within the range from 0.4 bar to 1.1 bar, more preferably at about 1 bar.

The treatment with the stripping gas is preferably effected at atmospheric pressure (standard pressure). However, for the purpose of optimization of the amount of stripping gas, stripping is in principle also possible under reduced pressure or particularly at slightly elevated pressure.

With regard to the gas used in the stripping (stripping gas), it is possible here to use a wide variety of different gases. In general, in process step (b), the stripping gas used is a gas which is non-reactive with respect to dinitrotoluenes and/or inert with respect to the nitrotoluenes. More particularly, the stripping gas may be selected from the group of nitrogen, oxygen, noble gases (preferably helium and argon), hydrogen, carbon oxides (e.g. carbon monoxide and carbon dioxide) and mixtures thereof (especially air as a nitrogen/oxygen mixture), preferably from the group of nitrogen, oxygen, noble gases and mixtures thereof, more preferably from the group of nitrogen, oxygen and mixtures thereof. Very particular preference is given to using nitrogen or air as a stripping gas, since these are the stripping gases that are the least expensive and have the best industrial availability.

The specific selection of the stripping gas also depends more particularly on which impurities or substances are to be removed from the DNTs to be treated: if, for example, a carbon oxide-free pure DNT is to be provided, the person skilled in the art will of course resort only to those among the aforementioned stripping gases which are free of carbon oxides.

In a typical embodiment of the process of the invention, the stripping gases used for the stripping of the washed DNTs may especially be all inert gases (i.e. all gases that are non-reactive with respect to the washed DNTs under stripping gas treatment conditions), more particularly provided that they are available inexpensively, for example air, nitrogen, noble gases, $CO_2$, CO, $N_2O$, hydrogen etc. Preference is given to using air or nitrogen, but it is also possible to use other stripping gases, taking particular regard of the stripping gas treatment parameters that are to be observed, such as pressure and temperature in particular, the DNT being laden in each case with the stripping gas up to its solubility limit with regard to Henry's law.

In general, the stripping gas should be at least essentially free of water and/or water vapor, especially at least essentially free of water vapor. In other words, in general, in process step (b), the stripping gas should not contain any water and/or any water vapor, especially any water vapor. This means that, in process step (b), the stripping is conducted in the absence of water and/or water vapor, especially in the absence of water vapor, or no water vapor is used as stripping gas in process step (b).

Nevertheless, an alternative possibility in principle is loading of the stripping gas with a (relative) air humidity or residual moisture content of up to 100% by weight, especially up to 90% by weight, preferably up to 70% by weight or less, especially based on stripping gas treatment temperature, preferably based on a gas temperature of 20° C. to 30° C.

This is because, as the applicant has found, the use of water vapor as stripping gas is detrimental in relation to the process of the invention for various reasons: firstly, the use of water vapor as stripping gas would introduce water into the DNTs to be treated. However, for safety reasons as well, water vapor is unsuitable or not of good suitability for the stripping within the process of the invention. A further disadvantage of stripping with water vapor is that—as well as the stripping gas with the impurities removed—a DNT/water mixture is always also obtained in the column bottom of the stripping column, which again has to be removed, such that an additional waste stream would be obtained as well as additional technical complexity. Therefore, water vapor as stripping gas should be avoided (even though it is usable in principle from a clinical point of view or is implementable in principle in terms of its use for performance of the process of the invention).

Water vapor is thus unsuitable or not particularly suitable as stripping gas—especially with regard to the preferred temperature ranges for stripping gas treatment, which should be noted for safety reasons: stripping with water vapor in the preferred temperature range of 105° C. or less is very complex from a technical point of view for a DNT melt to be treated with stripping gas under reduced pressure. A further disadvantage of the stripping of a DNT melt with saturated steam is that—as outlined above—not only the stripping gas together with the volatile impurities removed but always also a DNT/water mixture is obtained in the column bottom of the stripping column, which has to be removed; the strong and medium-strength acids still present in the DNTs to be stripped, such as nitric acid, trinitrocresols and nitrobenzoic acids, have to be extracted into this water obtained in the column bottom. Consequently, an additional waste stream is obtained, the handling of which is complex from a chemical engineering point of view. Consequently, in accordance with the invention, the stripping gas to use is free of water vapor.

Preferably, the stripping gas is used in dry or dried form (i.e. at least essentially free of water), especially since the stripping gas treatment is also supposed to reduce the residual water content in the DNT to be stripped. An alternative possibility in principle is loading of the stripping gas with a (relative) air humidity or residual moisture content of up to 100% by weight, especially up to 90% by weight, preferably up to 70% by weight or less, especially based on stripping gas treatment temperature, preferably based on a gas temperature of 20° C. to 30° C.

The amount of stripping gas used in process step (b) may vary within wide limits.

More particularly, in process step (b), the amount of stripping gas used is chosen and/or set depending on the stripping conditions, especially temperature and/or pressure and/or duration of the stripping and/or nature of the stripping gas, and/or depending on the content and/or nature of impurities in the dinitrotoluenes to be treated in process step (b) and/or depending on the target residual content of impurities in the nitrotoluenes that result after process step (b).

In a typical embodiment of the present invention, the amount of stripping gas to be used, for example calculated as the weight ratio of stripping gas to DNTs, can be chosen and/or set depending on the temperature and pressure at which the stripping is effected, and depending on the desired residual content of the individual impurities.

In a particular embodiment, in process step (b), the amount of stripping gas used, based on 1 metric ton of dinitrotoluenes to be treated and calculated as the volume of stripping gas in standard cubic meters under standard conditions (pressure of 1.01325 bar; air humidity of 0%, i.e. dry stripping gas; temperature of 0° C. [standard conditions according to DIN 1343, STPD]), is 0.1 to 1000 standard cubic meters of stripping gas, especially 0.5 to 500 standard cubic meters, preferably 1 to 200 standard cubic meters, more preferably 2 to 120 standard cubic meters, even more preferably 5 to 80 standard cubic meters, more preferably still 10 to 60 standard cubic meters.

The standard cubic meter (also referred to synonymously as normal cubic meter) is a unit of measurement used in chemical engineering and gas technology for an amount of gas. It describes that amount of gas that a volume of gas of one cubic meter would occupy under fixed conditions (temperature, pressure, air humidity). The standard cubic meter unit or the conversion to standard cubic meters is used in order to base figures stated in connection with gases on a comparable unit of measurement in an arbitrarily fixed but exactly defined state with regard to temperature, pressure and moisture content. In the context of the present invention, the unit of measurement of the standard cubic meter is used in relation to standard conditions or normal conditions (pressure of 1.01325 bar; air humidity of 0%, i.e. dry stripping gas; temperature of 0° C. [standard conditions according to DIN 1343, STPD]).

A standard cubic meter in the context of the present invention is thus that amount of gas which, at a pressure of 1.01325 bar and an air humidity of 0% by weight (dry stripping gas) and a temperature of 273.15 K (0° C.), has a volume of one cubic meter of gas.

One standard cubic meter (ideal gas) contains a constant molar amount of 44.615 mol of gas molecules (irrespective of the type of gas).

One standard cubic meter of the following gas types contains the following amounts of gases:
air: 1.293 kg
nitrogen: 1.250 kg
hydrogen: 0.0899 kg In a particular embodiment, in process step (b), the amount of stripping gas used, based on 1 metric ton of dinitrotoluenes to be treated and calculated as the volume of nitrogen as stripping gas under standard conditions (pressure of 1.01325 bar; air humidity of 0%, i.e. dry stripping gas; temperature of 0° C. [standard conditions according to DIN 1343, STPD]), may be 0.5 to 500 kg, especially 1 to 250 kg, preferably 1 to 140 kg, more preferably 5 to 50 kg, even more preferably 10 to 40 kg. If other inert gases are employed, the values reported for nitrogen as stripping gas should be adjusted or recalculated correspondingly.

In general, in process step (b), there is likewise drying and/or a reduction in the water content of the treated dinitrotoluenes. More particularly, in this context, the water content in the dinitrotoluenes that result after process step (b) is not more than 1% by weight, especially not more than 0.8% by weight, preferably not more than 0.5% by weight, more preferably not more than 0.4% by weight, even more preferably not more than 0.3% by weight, more preferably still not more than 0.2% by weight, based in each case on the dinitrotoluenes.

In general, in process step (b), the water content in the resulting dinitrotoluenes is lowered to such a degree that no further water is separated out in the course of cooling of the liquid dinitrotoluenes down to their solidification point.

In the treatment of a DNT washed in process step (a) with the inert gases, for example air or nitrogen, in a stripping unit, what is removed is thus not only low-boiling aliphatic and aromatic hydrocarbons, hydrogen cyanide, ammonia, nitric acid etc. and the impurities in the DNT that are already gaseous at room temperature, for example CO, $N_2O$, $CO_2$, NO, $NO_2$ etc., and the nitric acid newly formed from $NO_X$ in the presence of water, but also the water dissolved and possibly suspended in the DNT.

The proportion of still-dissolved water in the DNT after treatment with stripping gas is so low, or should be reduced after treatment with the stripping gas to such a degree, that no further water can be separated out in the course of cooling of the liquid DNT down to its melting point and hence the "dew point" cannot be attained. Thus, the formation of traces of water in an intermediate DNT storage facility, which is highly corrosive because of the residual acidity always present in the washed and stripping gas-treated DNT, is reliably avoided.

In a particular embodiment, in process step (b), the stripping may follow a preceding acidic, basic or neutral wash in process step (a). This means that, within the process of the invention, the upstream wash in process step (a) can be effected in one, two or three steps or may comprise one, two or three wash steps. For example, the treatment with the stripping gas may follow a first wash step (acidic wash) and/or a second wash step (alkaline wash) and/or a third wash step (neutral wash); this will be discussed in detail in connection with the figure illustrations discussed hereinafter and the working examples. However, treatment with a stripping gas is also possible after individual extraction stages or individual wash stages of the various wash steps.

In a particular embodiment of the present invention, after performance of process step (b), the stripping gas laden with the impurities removed from the dinitrotoluenes can be subjected to an offgas treatment, especially a thermal offgas treatment.

In an alternative embodiment to this, after performance of process step (b), the stripping gas laden with the impurities removed from the dinitrotoluenes can be subjected to a treatment for removal of the impurities from the laden stripping gas, preferably by means of condensation and/or washing with a preferably aqueous wash medium, optionally followed by recycling of the purified stripping gas into process step (b).

For example, the stripping gas, after removal of the impurities that can easily be condensed or easily washed out, for example nitric acid, hydrogen cyanide etc., and the aliphatic and aromatic hydrocarbons that are liquid at room temperature can be circulated, with advantageous discharge of a substream of the stripping gas laden with inert substances that cannot be condensed or washed out, such as CO, $N_2O$, etc., and sent to an offgas treatment, for example a thermal offgas treatment, in order to prevent enrichment of these inert substances in the stripping gas stream.

All impurities removed from the previously washed DNTs with the stripping gas and also the water removed are present in the offgas stream. This offgas stream can be sent, for example, without intermediate condensation to a thermal offgas treatment, when it is ensured that the water removed from the DNTs does not condense. Alternative possibilities are an intermediate condensation or an additional wash with a wash medium, such as water or a wash acid, when the acids of good solubility in water, such as nitric acid, $NO_X$, hydrogen cyanide etc., and the hydrocarbons are to be removed from the offgas, in order that the burden on the thermal offgas treatment is reduced.

The wastewater obtained in an intermediate condensation or in an additional treatment of the offgas with a wash medium, said wastewater containing, in particular, nitric acid, hydrogen cyanide and other impurities of good water solubility, and also DNT and traces of hydrocarbons removed, can—alone or together with the vapor condensate from the concentration of the wash acid from the first wash step (i.e. acidic wash) of process step a), as described, for example, in EP 0 736 514 A1 or in EP 1 780 198 A1—be freed of the dissolved and suspended DNT by extraction with the aromatic to be nitrated (i.e. in the case of DNT with toluene). The hydrogen cyanide can be removed in the extracted wastewater directly, for example by treatment with oxidizing agents, or by stripping with steam together with the extractant. After neutralization, this contaminated wastewater can then be released either to a biological aftertreatment or directly to a receiving water body.

The hydrogen cyanide enriched in the stripping condensate from the contaminated wastewaters, before this condensate is likewise released into a wastewater treatment, has to be destroyed or bound by a treatment with oxidizing agents or other measures. A substream of the volatile hydrocarbons removed, which still contain traces of MNT and DNT, can be recycled into the wash.

Prior to release into the environment, the offgas is typically oxidized by a postcombustion and released.

As already explained above, it is possible by the process of the invention, in a technically simple and reliable manner, to efficiently remove at least essentially all or virtually all impurities from the crude dinitrotoluenes as obtained in a nitration of toluene conducted by adiabatic or isothermal means, for example, in the presence of a nitric acid/sulfuric acid nitrating acid mixture, including those impurities, especially also volatile impurities (but also other impurities, such as nonacidic or weakly acidic impurities) which cannot be removed directly, if at all, by conventional purification processes for crude dinitrotoluenes. It is surprisingly possible, especially by means of the downstream stripping gas treatment, additionally also to effectively remove, in an effective manner, trace impurities which can, however, severely impair the downstream further use or further processing of the dinitrotoluenes (for example, as catalyst poisons, can impair catalytic hydrogenation of the dinitrotoluenes).

The impurities to be removed from the crude dinitrotoluenes with the aid of the process of the invention may especially be selected from the group of mineral acids (especially sulfuric acid, nitric acid and nitrous acid), unconverted and/or partly converted reactants, nitrogen oxides, carbon oxides and nitrated and non-nitrated reaction by-products, and also degradation and oxidation products of the products and by-products that originate from the nitration (for example hydrogen cyanide etc.).

More particularly, the impurities to be removed from the crude dinitrotoluenes with the aid of the process of the invention may be selected from the group of (i) mineral acids, especially sulfuric acid, nitric acid and nitrous acid; (ii) organic acids, especially formic acid, acetic acid, oxalic acid, nitrobenzoic acids such as mono- and dinitrobenzoic acids, picric acid, hydrogen cyanide or the like; (iii) nitroaromatics, especially nitrophenols, such as mono-, di- and trinitrophenols, and nitrocresols, such as mono-, di- and trinitrocresols; (iv) nitrogen oxides, especially nitrogen monoxide (NO), nitrogen dioxide ($NO_2$) and dinitrogen oxide ($N_2O$); (v) carbon oxides, especially carbon monoxide (CO) and carbon dioxide ($CO_2$); (vi) hydrocarbons, especially aliphatic and cycloaliphatic hydrocarbons; (vii) unconverted or partly converted reactants, especially toluene.

As explained above, it is possible in an unexpected manner by the process of the invention to remove especially also (but not just) volatile impurities from the crude dinitrotoluenes to be purified. This is understood in the context of the present invention to mean especially (but without restriction) those compounds which have a higher volatility, especially a higher vapor pressure and/or a lower melting point, than the crude dinitrotoluenes to be purified. The reference parameter employed for volatility may especially be the vapor pressure of the dinitrotoluenes under standard conditions (i.e. pressure of 1.01325 bar; air humidity of 0% [standard conditions according to DIN 1343, STPD]) and/or the boiling point of the dinitrotoluenes under standard conditions (i.e. pressure of 1.01325 bar; air humidity of 0% [standard conditions according to DIN 1343, STPD]). As explained above, the volatile compounds which can be removed within the process of the invention include, for example, nitrogen oxides (e.g. NO, $NO_2$, $N_2O$ etc.), hydrocarbons (e.g. aliphatic or aromatic hydrocarbons etc.), carbon oxides (e.g. CO, $CO_2$ etc.), hydrogen cyanide etc.

As explained above, the process of the invention is associated with a multitude of advantages and special features which delimit the present invention from the relevant prior art:

In the context of the process of the invention, crude dinitrotoluenes obtained from an adiabatic or isothermal dinitration of toluene, which are first washed in one or more, especially in one to three, wash steps and hence contain only traces of nitric acid, nitrogen oxides $NO_X$ and sulfuric acid, but still contain considerable amounts of impurities of the aforementioned type that are difficult to wash out, are thus treated with a stripping gas. This treatment of the previously washed DNTs with a stripping gas removes at least essentially all or virtually all impurities having a low boiling point and consequently high partial pressures compared to the DNTs, especially the impurities that are already gaseous at room temperature and are present in the DNTs, for example CO, $CO_2$, $N_2O$, NO, $NO_2$ etc., but also all impurities having low boiling points, for example hydrogen cyanide, nitric acid, aliphatic and aromatic hydrocarbons, water etc., which cannot be removed at all by a wash with water through a multistage liquid/liquid extraction, according to their partial pressures under Henry's law, in an effective manner and without any great technical complexity, completely or in a controlled manner down to the desired residual contents.

The process of the invention is advantageous particularly when, within the wash in process step (a), higher ratios of DNTs to be washed to freshly added wash medium are employed and/or when the impurities having small extraction coefficients to be removed from the crude DNTs are removable from the DNTs by physical means only by a multistage wash.

A further advantage of the process is that it is executable in an extremely flexible manner, since, in a multistage wash or a wash having several wash steps (e.g. wash having three wash steps), each wash step, after phase separation, may be followed by treatment of the DNTs with a stripping gas: in the process of the invention, it is possible to free either a DNT which has been washed in three wash steps and may still contain residual traces of hydrogen cyanide, ammonia (with ammonia as base in the alkaline or second wash step) and in particular relatively large amounts of neutral substances such as CO, $N_2O$ etc., and low-boiling aliphatic and aromatic hydrocarbons, and additionally considerable residual amounts of $NO_X$, or a DNT from the first or acidic wash step (treated with a wash acid, as described, for example, in EP 0 297 312 A1, EP 0 736 514 A1 or EP 1 780 195 A1) which additionally still contains nitrophenols, nitrocresols, nitrobenzoic acids as well as all impurities having unfavorable partition coefficients, low solubility in the wash medium, weak or zero acidity, for example CO, $CO_2$, hydrogen cyanide, $NO_X$, $N_2O$ etc., and also impurities of which some are hazardous catalyst poisons, and also low-boiling aliphatic and aromatic hydrocarbons etc. in a relatively large amount, of these impurities in a simple and efficient manner. Alternatively, a DNT after the second wash step (i.e. after the alkaline wash) can be efficiently treated with a suitable stripping gas. Alternatively, after every extraction stage of a wash step consisting of several extraction stages, a treatment of the DNT obtained after removal of the wash medium with a stripping gas is possible.

The process of the invention thus works reliably, safely, efficiently and flexibly from a technical point of view and is easily implementable in apparatus terms, but is simultaneously also economical in terms of its operation.

The two other aspects of the present invention—apparatus (plant) of the invention for purification of crude dinitrotoluenes resulting from the nitration of toluenes in the presence of a nitric acid/sulfuric acid nitrating acid mixture on the one hand (second aspect of the invention) and production plant of the invention for preparation of dinitrotoluenes on the other hand (further aspect of the invention)—are described hereinafter, wherein the reference numerals specified hereinafter relate to the figure illustrations according to the application as per FIGS. 1 to 4, which will be elucidated in detail once again hereinafter.

The present invention relates—in a second aspect of the present invention—to an apparatus (plant) for purification of crude dinitrotoluenes resulting from the nitration of toluene in the presence of a nitric acid/sulfuric acid nitrating acid mixture after removal of the spent nitrating acid mixture (also referred to synonymously as spent nitrating acid), especially for removal of volatile impurities in particular from the crude dinitrotoluenes as well, especially an apparatus (plant) for performance of a process according to the present invention as described above, wherein the apparatus comprises:

(a) at least one wash unit WE for washing the crude dinitrotoluenes R-DNT with at least one wash medium WM; and (b) arranged downstream of the wash unit WE, at least one stripping unit (stripping apparatus) SK for stripping (stripping gas treatment) of the washed dinitrotoluenes W-DNT; DNT-I, DNT-II, DNT-III coming from the wash unit WE with at least one gas (stripping gas) SG.

In a particular embodiment of the present invention, in the apparatus of the invention, the wash unit WE may have one or more, especially one, two or three, preferably three, wash units WS-I, WS-II, WS-III for washing the crude dinitrotoluenes R-DNT, especially a wash unit WS-I for conducting an acidic wash and/or a wash unit WS-II for conducting an alkaline wash and/or a wash unit WS-III for conducting a neutral wash.

In a preferred embodiment of the present invention, in the apparatus of the invention, the wash unit WE may have three wash units WS-I, WS-II, WS-III for washing the crude dinitrotoluenes R-DNT, comprising a wash unit WS-I for conducting an acidic wash, a wash unit WS-II, arranged downstream of the wash unit WS-I for conducting the acidic wash, for conducting an alkaline wash, and a wash unit WS-III, arranged downstream of the wash unit WS-II for conducting the alkaline wash, for conducting a neutral wash.

In one embodiment of the present invention, in the apparatus of the invention, the wash unit WE additionally may comprise at least one removal unit for removal of spent wash medium (WL) and/or wash medium (WL) laden with impurities removed from the dinitrotoluenes from the washed dinitrotoluenes W-DNT; DNT-I, DNT-II, DNT-III.

In a particular embodiment of the present invention, the stripping unit SK, especially a stripping column, may have a lower end (lower section) KS, especially a column bottom, and an upper end (upper section) KK, especially a column head, and a feed unit, preferably arranged at the lower end KS, for the stripping gas and a feed unit, preferably arranged at the upper end KK, for the washed dinitrotoluenes W-DNT; DNT-I, DNT-II, DNT-III.

Preferably, the stripping unit SK may take the form of a stripping column having a column bottom KS as the lower end (lower section) and a column head KK as the upper end (upper section). The stripping column may comprise a feed unit, preferably arranged at the column bottom KS, for the stripping gas SG and a feed unit, preferably arranged at the column head KK, for the washed dinitrotoluenes W-DNT; DNT-I, DNT-II, DNT-III.

In a particular embodiment of the present invention, the stripping unit SK may be configured such that the stripping unit SK, in the operating state, enables firstly counter- and/or crosscurrent flow, preferably countercurrent flow, of washed dinitrotoluenes W-DNT; DNT-I, DNT-II, DNT-III on the one hand and stripping gas SG on the other hand.

For further details relating to the apparatus (plant) of the invention, for avoidance of unnecessary repetition, reference may be made to the above details relating to the process of the invention, which apply correspondingly in relation to the apparatus (plant) of the invention.

The present invention relates—in a third aspect of the present invention—to a production plant for preparation of dinitrotoluenes, especially a production plant for nitration (dinitration) of toluene to give dinitrotoluenes in the presence of a nitric acid/sulfuric acid nitrating acid mixture with subsequent purification of the crude dinitrotoluenes that originate from the nitration, wherein the production plant comprises:

(i) a nitrating unit NE for nitration (dinitration) of toluene T in the presence of a nitric acid/sulfuric acid nitrating acid mixture MS to give dinitrotoluenes R-DNT, especially having one or more reaction vessels (nitration reactors) for performance of the nitration;

(ii) optionally, arranged downstream of the nitration unit NE in the production line, at least one removal unit, especially a separation unit (separator), for removal of the spent nitrating acid mixture SP from the crude dinitrotoluenes R-DNT;

(iii) arranged downstream of the nitration unit NE and of any removal unit present in the production line, an apparatus (plant) for purification for the crude dinitrotoluenes R-DNT, especially an apparatus (plant) according to the present invention as described above, comprising:

(a) at least one wash unit WE for washing the crude dinitrotoluenes R-DNT with at least one wash medium WM; and (b) arranged downstream of the wash unit WE, at least one stripping unit (stripping apparatus) SK for stripping (stripping gas treatment) of the washed dinitrotoluenes W-DNT; DNT-I, DNT-II, DNT-III coming from the wash unit WE with at least one gas (stripping gas) SG.

For further details relating to the production plant of the invention, for avoidance of unnecessary repetition, reference may be made to the above details relating to the process of the invention and to the apparatus (plant) of the invention, which apply correspondingly in relation to the production plant of the invention.

The details which now follow relate both to the apparatus (plant) of the invention and to the production plant of the invention.

Both in relation to the apparatus (plant) of the invention and in relation to the production plant of the invention, it may be the case that the stripping unit SK additionally comprises a heat exchanger WM1 for heating of the washed dinitrotoluenes W-DNT; DNT-I, DNT-II, DNT-III prior to introduction into the stripping unit SK. In addition, it may be the case that the stripping unit SK additionally comprises a heat exchanger WM2 for heating of the stripping gas SG prior to introduction into the stripping unit SK.

In addition, both in relation to the apparatus (plant) of the invention and in relation to the production plant of the invention, it may be the case that, arranged downstream of the stripping unit SK, an offgas treatment unit for the purification and/or treatment of the stripping gas laden with impurities removed from the dinitrotoluenes is provided. In one embodiment, the offgas treatment unit may comprise a wash unit WK, especially a wash column, optionally with a downstream, preferably thermal, offgas aftertreatment plant AB. In an alternative embodiment, the offgas treatment unit may comprise (only) a preferably thermal offgas treatment plant AB (i.e. without an upstream wash unit).

Other advantages, properties, aspects and features of the present invention will be apparent from the description of the embodiments preferred in accordance with the invention that are detailed in the description which follows of the figure illustrations according to FIGS. 1 to 4.

Figure 1:
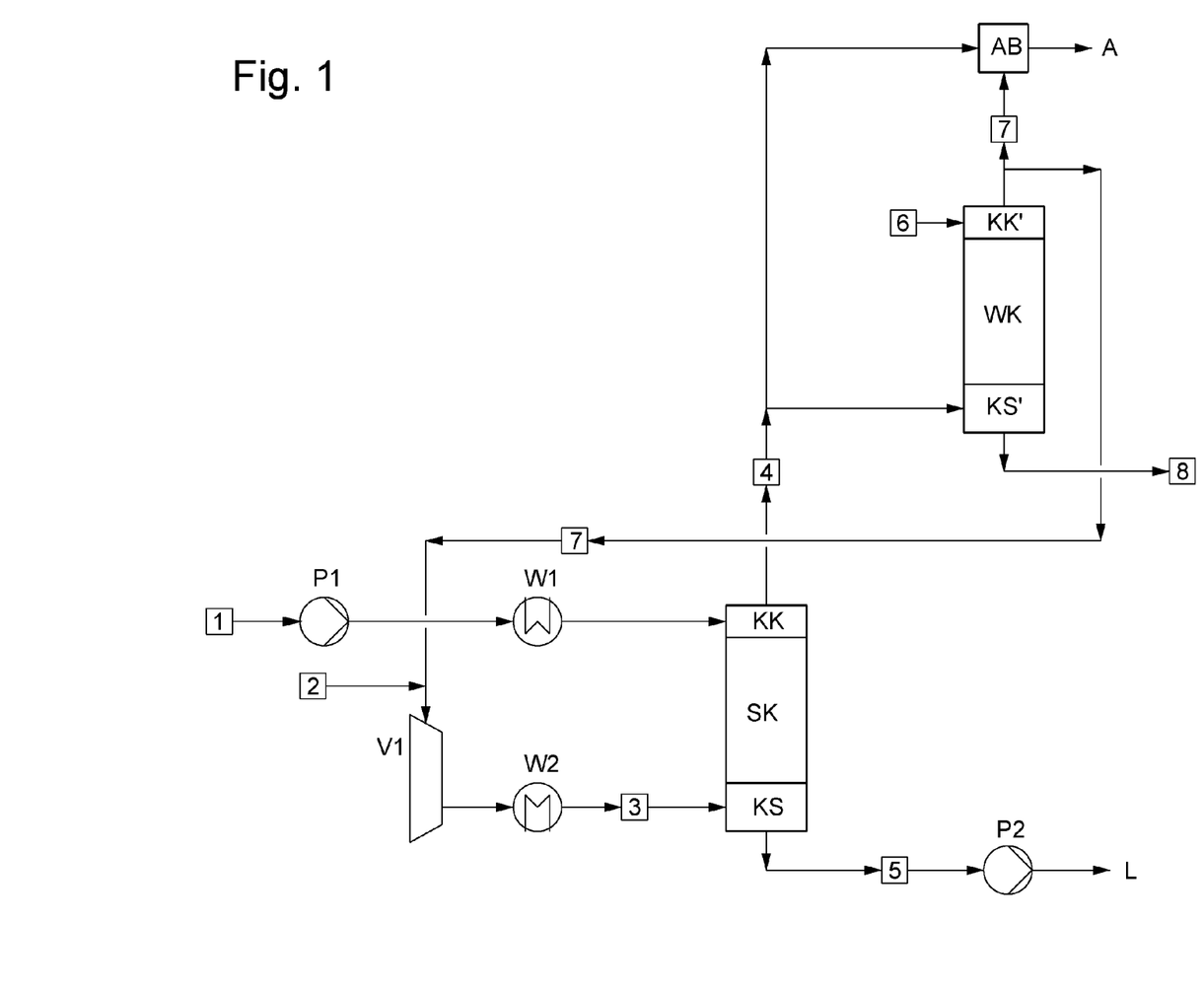
FIG. 1: a schematic diagram of a process of the invention and an apparatus (plant) of the invention for treatment of a DNT, previously treated with a wash medium, with a stripping gas in a preferred embodiment of the present invention.
Figure 2:
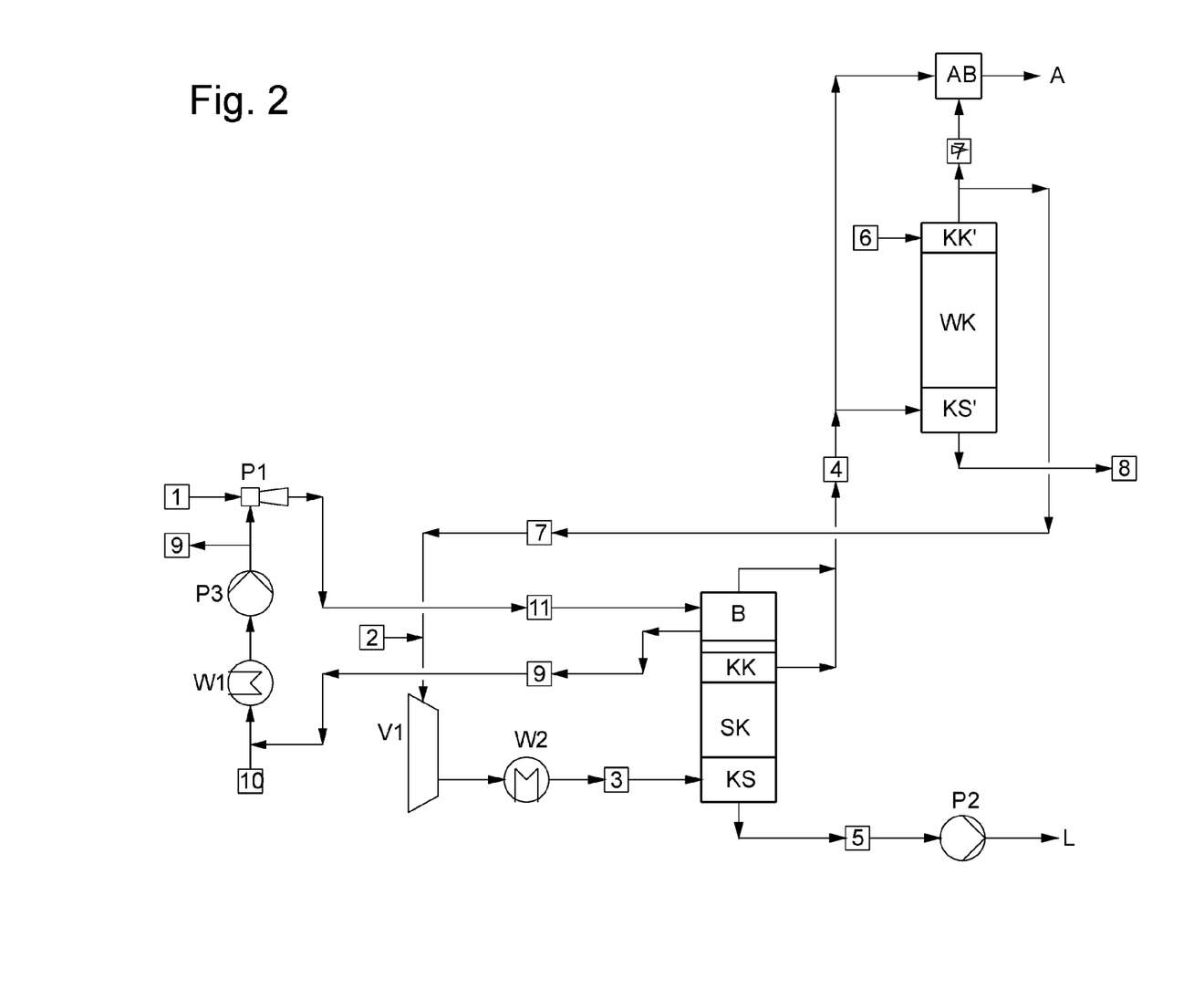
FIG. 2: a schematic diagram of a process of the invention and an apparatus (plant) of the invention for stripping of a DNT, previously treated with a wash medium, which has been supplied to the stripping unit by means of an injector, in a further preferred embodiment of the present invention.
Figure 3:
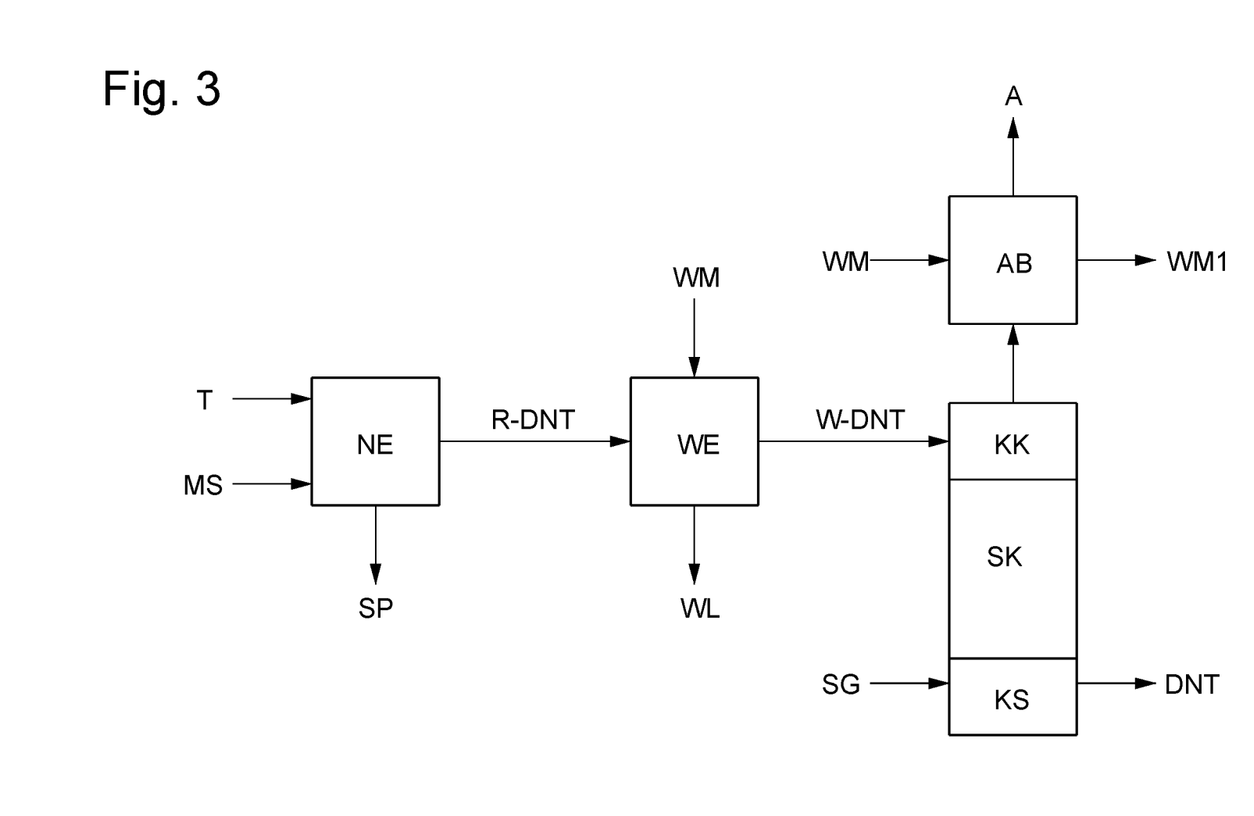
FIG. 3 a schematic diagram of a production plant of the invention comprising a nitration and a subsequent purification by means of washing of the DNT in conjunction with a stripping apparatus downstream of the wash, in a preferred embodiment of the present invention.
Figure 4:
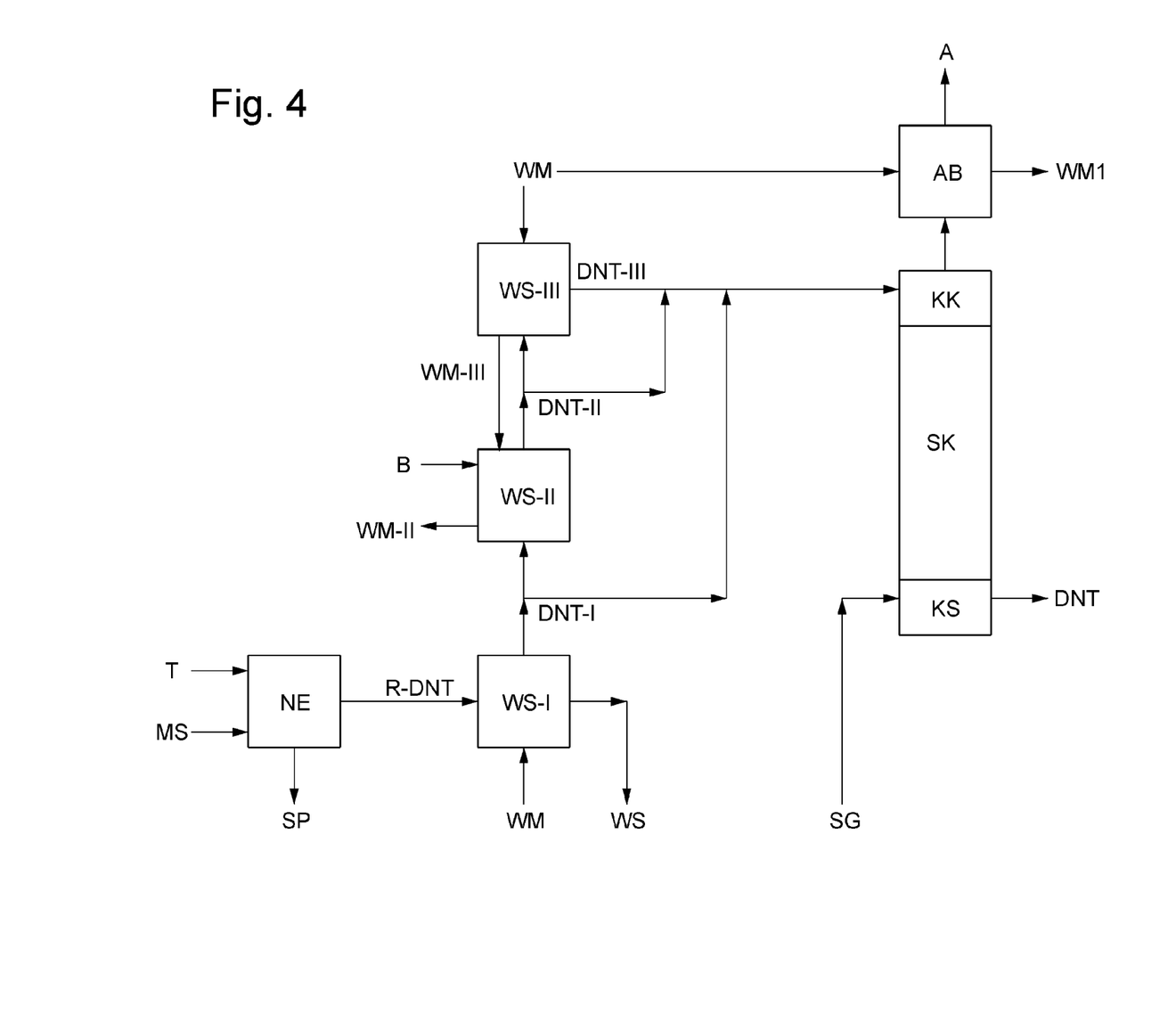
FIG. 4 a schematic diagram of a production plant of the invention comprising a nitration and a subsequent purification by means of washing of the DNT having three wash steps in conjunction with a stripping apparatus downstream of the wash, in a further preferred embodiment of the present invention.

The figures show:

FIG. 1: a schematic diagram of a process of the invention and an apparatus (plant) of the invention for treatment of a DNT, previously treated with a wash medium, with a stripping gas in a preferred embodiment of the present invention;

FIG. 2: a schematic diagram of a process of the invention and an apparatus (plant) of the invention for stripping of a DNT, previously treated with a wash medium, which has been supplied to the stripping unit by means of an injector, in a further preferred embodiment of the present invention;

FIG. 3 a schematic diagram of a production plant of the invention comprising a nitration and a subsequent purification by means of washing of the DNT in conjunction with a stripping apparatus downstream of the wash, in a preferred embodiment of the present invention;

FIG. 4 a schematic diagram of a production plant of the invention comprising a nitration and a subsequent purification by means of washing of the DNT having three wash steps in conjunction with a stripping apparatus downstream of the wash, in a further preferred embodiment of the present invention.

FIG. 1 shows a general example of the stripping of DNT with an inert gas. The material to be stripped (DNT) may be fed to the stripping unit, for example, by gravimetric means or else with a conveying unit suitable for conveying of DNT. The DNT 1 which has previously been treated with a wash medium may be fed to a heat exchanger W1 either by gravimetric means or with a pump P1 suitable for conveying of DNT. Downstream of the heat exchanger, the DNT 1 with the temperature envisaged for the stripping treatment arrives at the top KK of a stripping column SK. In the lower section of the stripping column SK, the column bottom KS, the heated stripping gas 3 is fed in simultaneously, which is adjusted to the temperature envisaged for the stripping treatment by means of a heat exchanger W2. After gravimetric passage of the stripping material (DNT 1) through the stripping column SK, the DNT 5 which has been freed of the volatile impurities is drawn off from the column bottom KS and flows either gravimetrically or by means of a pump P2 suitable for conveying of DNT into the intermediate storage facility L for the purified DNT 5.

The stripping gas 4 laden with the volatile compounds separated from the DNT is fed in in the lower section KS' of a wash column WK and cooled (for example to ambient temperature) and treated with the wash medium 6 applied in the column head KK' of the wash column WK. The stripping gas 7 which has been freed of the volatile impurities which can be condensed and washed out (such as DNT, hydrogen cyanide, nitric acid, volatile aromatic or aliphatic hydrocarbons, solvent residues etc.) is either circulated or released directly, or a substream thereof, to an offgas treatment plant AB, for example a thermal offgas treatment, and thence passes as cleaned offgas A into the environment. In the case of recycling of the stripping gas 7 or a substream thereof, the discharged portion is replaced by fresh gas 2 and recycled into the circuit via a fan V1. The wash medium 8 laden with the removed impurities that can be condensed and washed out, which has been drawn off from the column bottom KS' of the wash column WK, is—after removal of the dissolved and suspended product, for example by extraction with the aromatic to be nitrated—processed together with other wastewaters from the purification of the crude DNT such that it can be released or recycled into the nitration circuit.

FIG. 2 shows a specific embodiment of the process described in general terms in FIG. 1 or of the apparatus of the invention comprising an injector for transport of the DNT: the DNT 1 which has been treated with a wash medium is transported out of the wash unit with an injector P1 as an emulsion to the stripping column SK. The motive medium used for the injector P1 is the respective wash medium from the upstream wash, preferably the wash medium 10, which is supplied to the above-described wash steps I to III (acidic, basic and neutral wash). The emulsion 11 composed of DNT/motive medium is transported into the phase separation apparatus B, which may take the form of the upper section of the stripping column SK. The transport medium 9 removed, saturated with the nitroaromatic (DNT) and still containing traces of impurities dissolved in the DNT, after mixing with the envisaged amount of wash medium 10 and after passing through the heat exchanger W1, is recycled into the transport circuit as motive medium for the injector by means of pump P1. The excess water 9 from the motive medium circuit is fed into the wash as wash medium.

The DNT removed in the phase separation apparatus B flows gravimetrically to the head KK of the stripping column SK. In the lower portion of the stripping column SK, the column bottom KS, the heated stripping gas 3 is fed in simultaneously, which is adjusted to the temperature envisaged for the stripping treatment by the heat exchanger W2. After gravimetric passage of the stripping material (DNT) through the stripping column SK, the DNT 5 which has been freed of the volatile impurities is drawn off from the column bottom and flows either gravimetrically or by means of a pump P2 suitable for conveying of DNT into the intermediate storage facility L for the purified DNT 5.

The treatment of the stripping gas downstream of the stripping column SK, laden with the volatile impurities removed, is effected analogously to that described for FIG. 1.

FIG. 3 shows a general execution of a production plant of the invention for preparation of DNT from an adiabatic or isothermal nitration of toluene with integrated treatment of the washed DNT with a stripping gas.

The crude DNT R-DNT formed in the nitration unit NE by reaction of toluene T with a nitric acid/sulfuric acid nitrating acid mixture MS, after removal of the spent nitrating acid SP in the wash unit WE (for example for performance of the above-described wash steps I to III), is washed with a wash medium WM, preferably a wash acid, a wash alkali or water. The resulting wastewaters WL from the wash unit WE are worked up according to their origin, as described above.

The DNT W-DNT removed from the wash unit WE, from which the strong mineral acids such as sulfuric acid and nitric acid (wash step I) and all medium-strength acids having a $pK_A$ up to 8, such as trinitrocresols, nitrobenzoic acids, oxalic acid, $CO_2$ etc., have preferably been extracted, but which still contains the weak acids, such as hydrogen cyanide, and the inert substances, such as NO, CO, $N_2O$ or aliphatic or aromatic hydrocarbons, is applied in molten form to the head KK of the stripping unit/stripping column SK used in accordance with the invention and treated with the stripping gas SG which is introduced in the lower section/column bottom KS of the stripping unit SK. The DNT runs, for example gravimetrically, through the stripping unit SK and is withdrawn from the lower section KS of the stripping unit SK as pure product DNT. The stripping gas, laden with the impurities removed from the DNT, is cleaned in an offgas treatment plant AB, for example by washing with a wash medium and/or further offgas treatments, such as a removal of $NO_X$, and/or a thermal aftertreatment, in such a way that an offgas A that meets the applicable environmental regulations can be released. The wash medium WM1 which is drawn off at the base KS of the wash column WK contains—as well as traces of DNT—in dissolved or suspended form, all other condensable impurities which have been removed from the DNT in the stripping unit SK. Prior to release of the wash medium WM1 into a receiving water body, these substances are removed from the wash medium WM1.

FIG. 4 shows a specific embodiment of a production plant of the invention for preparation of DNT from an adiabatic or isothermal nitration of toluene according to FIG. 3 with the three customary wash steps of a wash of the DNT in conjunction with the integrated treatment, envisaged in accordance with the invention, of the DNT washed in wash steps I to III with a stripping gas. The crude DNT R-DNT formed in the nitration unit NE by reaction of toluene T with nitric acid in the presence of sulfuric acid MS, after removal of the spent nitrating acid SP, is washed in three wash steps WS-I, WS-II and WS-III, as described above.

In wash step I WS-I (acidic wash), the wash medium WM supplied is used to separate sulfuric acid and nitric acid in particular from the crude DNT, where the ratio of wash medium WM to product R-DNT to be washed is chosen such that the wash acid WS contains a content of acids of 10% to 40% by weight. After phase separation, the wash acid WS is recycled into the nitration directly or after concentration. The DNT DNT-I discharged from the wash step I WS-I is fed into the wash step II WS-II (alkaline wash) or else treated with a stripping gas SG.

In wash step II WS-II, by addition of a base B, for example to the wash medium WM-III supplied from wash step III WS-III, at a pH of the wash medium in the range from 8.5 to 9.5, the medium-strength and strong acids, such as trinitrocresols, nitrobenzoic acids, $CO_2$, oxalic acid etc., are removed. After phase separation, the alkaline wash medium WM-II is released into a wastewater treatment. The DNT DNT-II discharged from the wash step II WS-II is fed into the wash step III WS-III (neutral wash) or else treated with a stripping gas SG.

In the wash step III WS-III (neutral wash), the wash medium WM supplied is used to remove traces of wash medium WM-II and traces of impurities that are difficult to extract that are still present. After phase separation, the wash medium WM-III is fed into the wash step WS-II as wash medium. The DNT DNT-III discharged from the wash step III WS-III is treated with a stripping gas SG.

The DNTs DNT-I, DNT-II and DNT-III removed from the three wash steps WS-I, WS-II and WS-III are applied in molten form to the top KK of the stripping unit (stripping column) SK used in accordance with the invention and treated with the stripping gas SG which is introduced in the lower section (column bottom) KS of the stripping unit SK. The DNT (DNT-I to DNT-III) runs, for example, gravimetrically through the stripping unit SK and is withdrawn as pure product (DNT) from the lower section KS of the stripping unit SK. The stripping gas, laden with the impurities removed from the DNT, is cleaned in an offgas treatment plant AB by washing with a wash medium and/or further offgas treatments, such as a removal of $NO_X$, and/or a thermal aftertreatment, in such a way that an offgas A that meets the applicable environmental regulations can be released.

The wash medium WM1 which is drawn off at the base KS of the wash column also contains, as well as traces of DNT, in dissolved or suspended form, all other condensable impurities which have been removed from the DNT in the stripping unit SK. Prior to release of the wash medium WM1 into a receiving water body, these substances have to be removed.

Further configurations, alterations, variations, modifications or the like of the present invention will be immediately apparent to and implementable by the person skilled in the art on reading the description, without leaving the scope of the present invention.

The present invention is illustrated by the working examples which follow, but without restricting the present invention thereto.

WORKING EXAMPLES

Example 1 (Comparative)

A crude DNT (2900 kg/hour) containing about 14 kg of nitric acid, about 7.4 kg of nitrogen dioxide, about 0.37 kg of sulfuric acid and about 50 ppm of hydrogen cyanide per metric ton of crude DNT was washed in accordance with the prior art in three wash steps.

In the first wash step (acidic wash), in accordance with EP 0 736 514 A1/EP 1 780 198 A1, washing was effected with a DNT/water ratio of about 9:1 (based on weight). To maintain the defined DNT/wash acid phase ratio in the wash apparatuses, the wash acid was additionally circulated. The wash acid from this acidic wash with about 27.6% total acid, after concentration to about 60% total acid (determined as nitric acid), was recycled into the nitration. The vapor concentrate from the concentration was recycled into the acidic wash.

In the second wash step (alkaline wash), in the presence of sodium carbonate at pH 9.2, all nitrocresols, nitrobenzoic acids and all weak acids having $pK_A$ values two units less than the pH of the wash liquor were extracted fully from the DNT. Neutral substances, such as CO, $N_2O$, hydrocarbons etc. and very weak acids, such as hydrogen cyanide having a $pK_A$ of 9.2, were extracted only according to their solubility or only partly into the wash medium. To maintain the defined DNT/wash medium phase ratio in the wash apparatuses, the wash liquor was additionally circulated.

In the third wash step (neutral wash), washing was effected with a DNT/process water ratio of 2:1 (based on weight). To maintain the defined DNT/wash medium phase ratio in the wash apparatuses, the wash water was additionally circulated. The wash water from the neutral wash, after phase separation, was fed into the alkaline wash.

After this wash according to the prior art, a DNT was obtained, from which all acids that form salts in the alkaline range have been largely removed. As well as max. 2 ppm of sulfate, less than 10 ppm of nitrocresols (in the present case trinitrocresols) and less than 10 ppm of nitrobenzoic acids, also found were about 15 ppm of nitric acid (sum total of $HNO_3$ plus $HNO_2$), about 2 ppm of hydrogen cyanide, about 100 ppm of CO, about 5 ppm of $CO_2$, 50 ppm of $N_2O$, about 300 ppm of aliphatic hydrocarbons and about 1% water.

Example 2 (Inventive)

A DNT washed according to prior art (2800 kg/h), as described in example 1, was applied at 85° C. to the head of a stripping column with 10 trays and stripped with 45 standard cubic meters/h of nitrogen at a temperature of likewise 85° C. The DNT (temperature about 74° C.) that runs off at the base of the column still contained less than 2 ppm of nitric acid (sum total of $HNO_3$ plus $HNO_2$), less than 0.1 ppm of hydrogen cyanide and less than 5 ppm of $N_2O$, CO and $CO_2$ in total (and less than 10 ppm of aliphatic hydrocarbons). The water content fell to about 0.17%. Also present in the offgas, in addition to the impurities stripped out, was DNT, which was separated out in an intermediate condensation and treatment with a wash medium.

As demonstrated by inventive working example 2, the purity of the DNT obtained can be improved significantly over the purification process according to prior art (example 1); more particularly, it is also possible in accordance with the invention to remove the impurities that are not removable according to prior art in a simple and efficient manner.

Example 3 (Inventive)

A crude DNT (2900 kg/hour) containing about 14 kg of nitric acid, about 7.4 kg of nitrogen dioxide, about 0.37 kg of sulfuric acid and about 50 ppm of hydrogen cyanide per metric ton of crude DNT was washed in just one wash step (acidic wash only), in accordance with EP 0 736 514 A1/EP 1 780 198 A1, at a DNT/process water ratio of about 9:1 (based on weight). To maintain the defined DNT/wash acid phase ratio in the wash apparatuses, the wash acid was additionally circulated. The wash acid from this acidic wash with about 27.6% total acid and about 80 ppm of hydrogen cyanide, after concentration to about 60% total acid (determined as nitric acid), was recycled into the nitration. The vapor concentrate from the concentration with about 1.5% total acid (determined as nitric acid) and about 100 ppm of hydrogen cyanide was freed of still-dissolved DNT by extraction with toluene; the extractant was then removed from the vapor concentrate by stripping with steam together with other volatile substances, for example hydrogen cyanide, and the vapour condensate treated in this way, after neutralization, was released directly to a biological aftertreatment.

The DNT, after this acidic wash (about 2800 kg/h), still contained all the nitrocresols (predominantly trinitrocresols) and nitrobenzoic acids present in the crude DNT, about 2 ppm of sulfate, 650 ppm of nitric acid (sum total of $HNO_3$ plus $HNO_2$), 40 ppm of hydrogen cyanide, 150 ppm of CO, 40 ppm of $CO_2$, 60 ppm of $N_2O$, about 300 ppm of aliphatic hydrocarbons and about 1% water.

This DNT was applied at 85° C. to the head of a stripping column with 10 trays and stripped with 80 standard cubic meters/h of nitrogen at a temperature of likewise 85° C. The DNT (temperature: about 71° C.) that runs off at the base of the column still contained 30 ppm of nitric acid (sum total of $HNO_3$ plus $HNO_2$), max. 0.5 ppm of hydrogen cyanide and less than 10 ppm of $N_2O$, CO and $CO_2$ in total and less than 10 ppm of aliphatic hydrocarbons. The water content fell to about 0.2%. Also present in the offgas, in addition to the impurities stripped out, was DNT, which was separated out in an intermediate condensation and recycled.

As demonstrated by inventive working example 3, the procedure of the invention, even with only a one-stage wash, can considerably improve the purity of the DNT obtained compared to conventional prior art purification processes.

Example 4 (Comparative)

Example 3 was repeated, but with the alteration or reversal of the sequence of the treatment steps (upstream stripping gas treatment with subsequent wash):

First of all, the stripping gas treatment was conducted in accordance with example 3 and only then the acidic wash in accordance with example 3. Two nitric acid waste streams were obtained (namely in the offgas of the stripping and in the wash water). The DNT thus obtained contained—as well as all the nitrocresols (predominantly trinitrocresols) and nitrobenzoic acids present in the crude DNT—about 3.0 ppm of sulfate, 1200 ppm of nitric acid (sum total of $HNO_3$ plus $HNO_2$), 35 ppm of hydrogen cyanide, 110 ppm of CO, 30 ppm of $CO_2$, 35 ppm of $N_2O$, about 250 ppm of aliphatic hydrocarbons and about 1.2% water. As demonstrated by example 4, it is not possible to achieve an efficient purifying effect with an altered sequence of treatment (stripping before wash).

The invention claimed is:
1. A process for purifying crude dinitrotoluenes resulting from the nitration of toluene in the presence of a nitric acid/sulfuric acid nitrating acid mixture
wherein the process comprises the following steps:
(a) the crude dinitrotoluenes, after separation from the spent nitrating acid mixture, are first subjected to a washing with at least one wash medium, followed by a removal of the wash medium; and (b) subsequently, the washed dinitrotoluenes resulting from process step (a) are subjected to a stripping via stripping gas treatment with at least one stripping gas, wherein the stripping gas used is a gas which is non-reactive with respect to dinitrotoluenes and is selected from the group consisting of nitrogen, oxygen, noble gases, hydrogen, carbon oxides and mixtures thereof and wherein the stripping is conducted in the absence of steam.

2. The process as claimed in claim 1,
wherein, in process step (a), the wash is conducted as a liquid/liquid extraction and wherein, in process step (a), the wash is conducted in one or more wash steps.

3. The process as claimed in claim 1,
wherein, in process step (a), the wash is conducted in three wash steps, wherein the wash in three wash steps comprises a first acidic wash step, a subsequent second alkaline wash step and a final third neutral wash step.

4. The process as claimed in claim 1,
wherein, in process step (b), the stripping is conducted in a stripping apparatus.

5. The process as claimed in claim 1,
wherein, in process step (b), the stripping is conducted in crosscurrent and/or countercurrent.

6. The process as claimed in claim 1,
wherein, in process step (b), the stripping is conducted at temperatures above the melting temperature of the dinitrotoluenes.

7. The process as claimed in claim 1,
wherein, in process step (b), the stripping is conducted at temperatures within a temperature range from 56° C. to 130° C.

8. The process as claimed in claim 1,
wherein, in process step (b), the amount of stripping gas depends on the stripping conditions.

9. The process as claimed in claim 1, wherein, in process step (b), the amount of stripping gas used, based on 1 metric ton of dinitrotoluenes to be treated and calculated as the volume of stripping gas in standard cubic meters under standard conditions, pressure of 1.01325 bar; air humidity of 0%; temperature of 0° C., standard conditions according to DIN 1343, STPD, is 0.1 to 1000 standard cubic meters of stripping gas.

10. The process as claimed in claim 1, wherein, in process step (b), the amount of stripping gas used, based on 1 metric ton of dinitrotoluenes to be treated and calculated as the amount of nitrogen as stripping gas under standard conditions, pressure of 1.01325 bar; air humidity of 0%; temperature of 0° C., standard conditions according to DIN 1343, STPD, is 0.5 to 500 kg.

* * * * *